(12) United States Patent
Samproni

(10) Patent No.: US 12,320,771 B2
(45) Date of Patent: Jun. 3, 2025

(54) SYSTEM AND METHOD OF MEASUREMENT AND CALIBRATION OF ANALYTE TESTING

(71) Applicant: Siemens Healthcare Diagnostics Inc., Tarrytown, NY (US)

(72) Inventor: Jennifer Samproni, Braintree, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 705 days.

(21) Appl. No.: 17/617,866

(22) PCT Filed: Jun. 5, 2020

(86) PCT No.: PCT/US2020/036312
§ 371 (c)(1),
(2) Date: Dec. 9, 2021

(87) PCT Pub. No.: WO2020/251848
PCT Pub. Date: Dec. 17, 2020

(65) Prior Publication Data
US 2022/0236209 A1    Jul. 28, 2022

Related U.S. Application Data

(60) Provisional application No. 62/860,487, filed on Jun. 12, 2019.

(51) Int. Cl.
*G01N 27/333* (2006.01)
*G01N 27/30* (2006.01)
(Continued)

(52) U.S. Cl.
CPC ........ *G01N 27/333* (2013.01); *G01N 27/301* (2013.01); *G01N 27/4163* (2013.01); *G01N 33/492* (2013.01)

(58) Field of Classification Search
CPC ............... G01N 27/333; G01N 27/301; G01N 27/4163; G01N 27/4035; G01N 27/403; G01N 33/492
See application file for complete search history.

(56) References Cited

U.S. PATENT DOCUMENTS 3,607,702 A * 9/1971 Haller .................... G01N 27/36
204/420
3,856,649 A * 12/1974 Genshaw ........... G01N 27/3335
204/418

(Continued)

FOREIGN PATENT DOCUMENTS

EP       0772041 A1    5/1997
WO   2013163120 A1   10/2013

OTHER PUBLICATIONS

International Search Report and Written Opinion of International Application No. PCT/US2020/036312 dated Oct. 15, 2020.

(Continued)

*Primary Examiner* — Alexander S Noguerola

(57) ABSTRACT

The inventive concepts disclosed herein are generally directed to the need to measure a microsample and obtain one or more measurement for one or more analyte in the microsample by configuring a sensor array having one or more first reference signal source interlaced with one or more analyte sensor positioned along the longitudinal axis the sensor body and a second reference signal source positioned downstream of the sensor body along a sample flow path.

12 Claims, 5 Drawing Sheets

(51) Int. Cl.
*G01N 27/416* (2006.01)
*G01N 33/49* (2006.01)

(56) References Cited

U.S. PATENT DOCUMENTS

| | | | | |
|---|---|---|---|---|
| 4,002,547 | A | * | 1/1977 | Neti .................. G01N 27/301 |
| | | | | 204/296 |
| 4,461,998 | A | | 7/1984 | Kater |
| 4,627,893 | A | | 12/1986 | Cormier et al. |
| 5,132,000 | A | * | 7/1992 | Sone .................. G01N 33/96 |
| | | | | 205/787.5 |
| 5,165,406 | A | * | 11/1992 | Wong ................ A61B 5/15003 |
| | | | | 600/366 |
| 5,336,388 | A | | 8/1994 | Leader et al. |
| 6,599,409 | B1 | * | 7/2003 | Broadley ............. G01N 27/401 |
| | | | | 204/408 |
| 2005/0241959 | A1 | * | 11/2005 | Ward .................. G01N 27/4146 |
| | | | | 205/792 |
| 2006/0065527 | A1 | | 3/2006 | Samproni |
| 2009/0101524 | A1 | * | 4/2009 | Woodward ............. G01N 27/36 |
| | | | | 204/406 |
| 2012/0090993 | A1 | | 4/2012 | Mansouri et al. |
| 2014/0273187 | A1 | | 9/2014 | Johnson et al. |
| 2015/0101938 | A1 | | 4/2015 | Bychkova et al. |
| 2017/0203294 | A1 | | 7/2017 | Samproni |
| 2018/0070869 | A1 | | 3/2018 | Ionescu et al. |
| 2018/0259543 | A1 | | 9/2018 | Gan |
| 2018/0284049 | A1 | | 10/2018 | Zhang et al. |

OTHER PUBLICATIONS

Van den Berg et al., "A Micro-Volume Open Liquid-Junction Reference Electrode for pH-ISFETs", Jan. 1990, Sensors and Actuators: B. Chemical, vol. 1, pp. 425-432.

* cited by examiner

SYSTEM AND METHOD OF MEASUREMENT AND CALIBRATION OF ANALYTE TESTING

This application claims priority to U.S. Provisional Application No. 62/860,487, filed Jun. 12, 2019, the disclosure of which is hereby incorporated by reference in its entirety.

FIELD OF THE DISCLOSURE

The disclosure generally relates to systems and methods having a sensing device within a sample path that is configured to test a variety of analytes using a first sample volume, and a second sample volume with the first sample volume being greater than the second sample volume. More particularly the disclosure relates to systems and methods allowing for an individual test or multiple tests to be run concurrently using the second sample volume.

BACKGROUND

Previous sensor array assemblies are useful in chemistry and medicine to determine the presence and concentration of a biological analyte. For example, various types of analytical tests related to patient diagnosis and therapy can be performed by analysis of a liquid sample taken from a patient. Liquid samples commonly include bodily fluids such as urine, blood, plasma, saliva, cerebrospinal fluid, pleural fluid, nasopharyngeal and the like. Blood samples, for example, are routinely analyzed to obtain measurements of the partial pressures of $CO_2$ and $O_2$ and concentrations of electrolytes and metabolites in the blood.

Patients in intensive care units may require a sampling frequency of 15-20 per day for blood gas and clinical chemistry requirements. In these cases, analyzing small liquid samples is desirable due to the relatively large number of samples taken in a relatively short period of time. Further, to limit the number of tests performed, it is desirable to gather as much information as possible with each test.

A number of different analyzers currently exist for making such measurements utilizing rigid layered sensor assemblies and electrical circuits. Such sensor array assemblies are used to assess the condition of medical patients through primary clinical indications. Some prior art analyzers have a sensor array assembly having multiple sensors positioned on a wall of a flow channel. A fluidic path adjacent to the sensors may be created using a second material such as molded plastic which is bonded to the wall containing the sensors. The liquid sample is passed through the fluidic path to interact with the sensors. Other sensor array assemblies for liquid sample analysis consist of multiple substrates with an intervening spacer acting to provide a fluid path.

Sensor array assemblies utilizing spacers generally are comprised of at least two sensors to detect analytes, and a reference signal source, to sense the measurement of the chosen one or more analyte in the liquid sample. In conventional sensors arrays, the reference electrode is located in the last position of the sensor array, and is referred to as an "open liquid junction" reference sensor. The open liquid junction reference sensor is placed at the last position in the sensor array due to potential contamination of the fluidic path. Additionally, the analyzer typically contains an electronic sensing and control apparatus for receiving readings from the sensors and the reference electrode, and determining a presence and/or concentration of one or more analyte of interest.

The prior art discloses the reference signal source being an electrochemical cell placed within the fluidic path downstream of the sensors to detect the analytes. The sensor is a device that measures a physical quantity and converts the physical quantity into a signal which may be read by an observer or an instrument. The sensor may work in a physiochemical manner using a sensing medium such as light, electricity, piezoelectric, electrochemical, or the like. The sensing medium can be read by a transducer or detector element that transforms the signal from the sensor into another signal that may be more easily measured and quantified. The signal produced by the transducer or detector element may be provided to a reader device having associated electronics, signal processors, and/or a display to provide the results in a user readable format. For example, the results may be provided on a graphical display.

Conventional types of reference signal sources include a reference electrode having a liquid junction wherein the sample meets the liquid junction. The junction is typically either open or constrained. In an open liquid junction system, the liquid junction operates by free diffusion. The open liquid junction allows an electrolyte in its entirety (liquid/gel and all) to make contact with the sample through the open liquid junction. Open liquid junctions of this type have moderate to high flow rates, provide low resistance and low junction potentials. In a constrained-diffusion junction system, a region of porous material permeable to water and salts (a membrane, porous plug, frit, or the like) is placed at the site of the liquid junction. The porous material acts as a constraint whereby passage of large molecules (such as protein) and bulk liquid is generally hindered. The open liquid junction solution typically contains a solution saturated with a salt which functions to reduce and maintain constant the interfacial potential which develops across the liquid junction boundary, typically referred to as a liquid junction potential. Because the reference signal source is placed downstream of the sensors, the liquid sample must traverse the sensors before traversing the reference signal source. This requires a substantial volume of liquid sample.

It is desirable to reduce the amount of liquid sample used to test the liquid sample for the presence and/or the concentration of a variety of analytes. It is to such an improved system and method that the present disclosure is directed.

SUMMARY

The inventive concepts disclosed herein are generally directed to the need to measure a low volume sample (e.g., a microsample) and obtain one or more measurement for one or more analyte in the low volume sample by configuring a sensor array having one or more first reference signal source positioned between two analyte sensors. A second reference signal source is spaced, e.g., downstream, from the first reference signal source in the sample flow path. The sensor body may have a first end, a second end, and a longitudinal axis extending between the first end and the second end of the sensor body. The analyte sensors may be spaced apart along the longitudinal axis. Further, the sample flow path may be directed from the first end towards the second end. The first reference signal source can be located at the first end of the sensor body, and the second reference signal source can be located at a last position within the sensor array. For example, the second reference signal source can be located at the second end of the sensor body, or beyond the second end of the sensor body. A first sample having a sufficient volume to traverse the sample flow path is moved through the sample flow path. As the first sample traverses the sample flow path, the first sample will come into contact with the analyte sensors, the first reference signal source, and the second reference signal source. The analyte sensors generate an analyte reading, the first reference signal source generates a first reference reading, and the second reference signal source generates a second reference reading. The second reference reading is used in conjunction with readings from the analyte sensors to obtain measurements from the analyte sensors. The second reference reading is also compared to the first reference reading to generate a calibration factor for calibrating the first reference reading. Thereafter, a second sample is passed through only a portion of the sample flow path so as to contact a subset of the analyte sensors and the first reference signal source, and without the second sample contacting the second reference signal source. In this event, a third reference reading from the first reference signal source is adjusted with the calibration factor, and then used to interpret and read analyte readings generated from analyte sensors within the subset. Thus, calibrating the first reference reading with the second reference reading allows the first reference signal source to be used to read samples that are passed through only a portion of the sample flow path and without requiring a sample volume to travel the entire sample flow path.

BRIEF DESCRIPTION OF THE DRAWINGS

The accompanying drawings, which are incorporated in and constitute a part of this specification, illustrate one or more implementations described herein and, together with the description, explain these implementations. The drawings are not intended to be drawn to scale, and certain features and certain views of the figures may be shown exaggerated, to scale or in schematic in the interest of clarity and conciseness. Not every component may be labeled in every drawing. Like reference numerals in the figures may represent and refer to the same or similar element or function. In the drawings.

DETAILED DESCRIPTION

Figure 1:
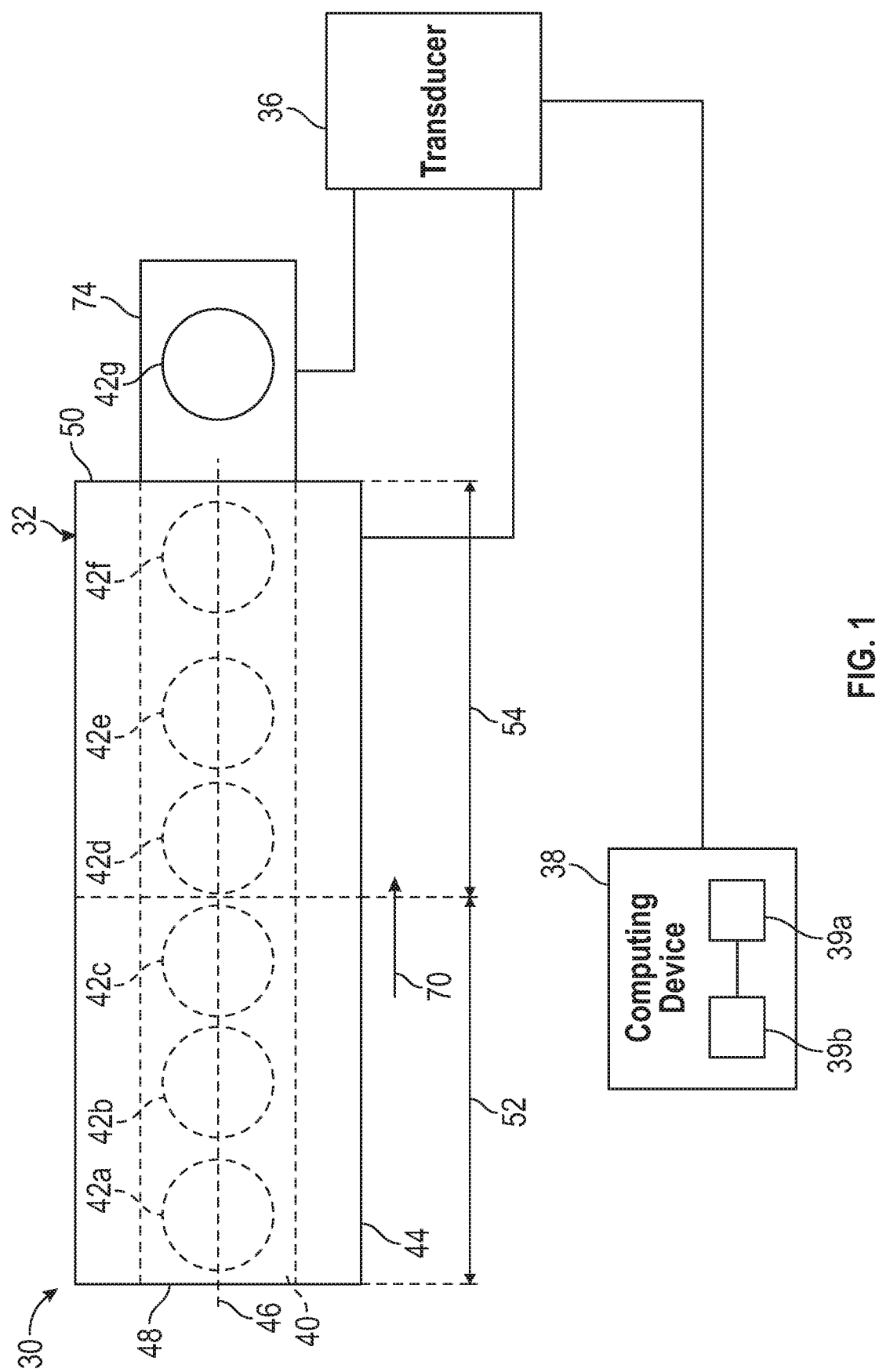
FIG. 1 is a general representation of an exemplary analyzer described herein.

The following detailed description refers to the accompanying drawings. The same reference numbers in different drawings may identify the same or similar elements.

The mechanisms proposed in this disclosure circumvent the problems described above. The present disclosure describes a system and method generally directed to the need to accurately measure one or more analyte in a low sample volume. Low sample volumes are desirable when a sample is limited, such as the case of neonatal or when the sample itself is expensive. As opposed to the prior art configurations, which required the sample volume to increase with the number of analytes being detected, the required sample volume can be reduced when a first reference signal source that is configured not to contaminate the sample is interlaced between at least two ion-selective analyte sensors and a second reference signal source that is configured to contaminate the sample is downstream of the last ion-selective analyte sensor. The ion-selective analyte sensors can be amperometric, potentiometric and combinations thereof. In some embodiments, the ion-selective analyte sensor has at least one electrode. Exemplary analytes to be detected can be, but are not limited to: glucose, lactate, creatinine, BUN, pH, $pCO_2$, $pO_2$, sodium, calcium, potassium, and chloride. The second reference signal source may be positioned at the end of a sensor body supporting the first reference signal source and the ion-selective analyte sensors to calibrate a potential of the first reference signal source. Then, the ion-selective analyte sensors can be measured by determining a measured potential difference between the ion-selective analyte sensors and the calibrated first reference signal source.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more and the singular also includes the plural unless it is obvious that it is meant otherwise.

Further, use of the term "plurality" is meant to convey "more than one" unless expressly stated to the contrary.

As used herein, qualifiers like "substantially," "about," "approximately," and combinations and variations thereof, are intended to include not only the exact amount or value that they qualify, but also some slight deviations therefrom, which may be due to manufacturing tolerances, measurement error, wear and tear, stresses exerted on various parts, and combinations thereof, for example.

As used herein, the term "sample" and variations thereof is intended to include biological tissues, biological fluids, chemical fluids, chemical substances, suspensions, solutions, slurries, mixtures, agglomerations, tinctures, slides, powders, or other preparations of biological tissues or fluids, synthetic analogs to biological tissues or fluids, bacterial cells (prokaryotic or eukaryotic), viruses, single-celled organisms, lysed biological cells, fixed biological cells, fixed biological tissues, cell cultures, tissue cultures, genetically engineered cells and tissues, genetically engineered organisms, and combinations thereof, for example.

The term "low sample volume" generally refers to a sample volume that is between a non-zero lower limit and 100 microliters. The size of the lower limit is dependent upon a number of analytes tested, the sensor size, and a size of the sample flow path. In some embodiments, e.g., for glucose strips which incorporate dry reagent chemistry, the lower limit of the sample volume may be 1 or 2 microliters. In other examples, including sensor assemblies having multiple sensors for analyzing blood, the lower limit may be 5 microliters.

The use of the term "at least one" or "one or more" will be understood to include one as well as any quantity more than one. In addition, the use of the phrase "at least one of X, V, and Z" will be understood to include X alone, V alone, and Z alone, as well as any combination of X, V, and Z.

The use of ordinal number terminology (i.e., "first", "second", "third", "fourth", etc.) is solely for the purpose of differentiating between two or more items and, unless explicitly stated otherwise, is not meant to imply any sequence or order or importance to one item over another or any order of addition.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

In the following detailed description of embodiments of the inventive concepts, numerous specific details are set forth in order to provide a more thorough understanding of the inventive concepts. However, it will be apparent to one of ordinary skill in the art that the inventive concepts within the instant disclosure may be practiced without these specific details. In other instances, well-known features have not been described in detail to avoid unnecessarily complicating the instant disclosure.

FIG. 1 depicts an embodiment of an analyzer 30 provided with a sensory array assembly (also referred to herein as an electrode array assembly) 32, a transducer 36, and a computing device 38. In general, the sensory array assembly 32 has a sample flow path 40 configured to receive a volume of a sample, and to pass the sample through at least a portion of the sample flow path 40. The sensory array assembly 32 is also provided with a plurality of sensors 42 that each generates a first signal indicative of a presence or absence of a particular analyte within the sample. The sensory array assembly 32 is shown by way of example as having seven sensors 42, and such sensors 42 are labeled with reference numerals 42a-g by way of example. The sensors 42 can be amperometric, potentiometric and combinations thereof. In some embodiments, the sensor 42 has at least one electrode. Exemplary analytes to be detected by particular ones of the sensors 42 can be, but are not limited to: glucose, lactate, and creatinine, Blood Urea Nitrogen ("BUN"), pH, pCO2, pO2, sodium, calcium, potassium, and chloride. In one embodiment, the sensors 42 are configured to measure pH, pCO2, O2, sodium, calcium, chloride, potassium, glucose, and lactate. It is desirable to position the sensors 42 in a manner so as to minimize sample volume between common diagnostic panels, such as pH and lactate. In one embodiment, one of the sensors 42 is a lactate sensor, and another one of the sensors 42 is a pH sensor. In this embodiment, the lactate sensor and the pH sensor may be located next to each other to minimize sample volume necessary to read both lactate and pH.

It should be understood that the sensory array assembly 32 should have at least three sensors 42 with at least one of the sensors 42 being an ion-selective analyte sensor; at least one of the sensors 42 being a first reference signal source, and at least one of the sensors being a second reference signal source. The second reference signal source is spaced a distance away from, e.g., downstream of, the ion-selective analyte sensor, and the first reference signal source so as to be able to complete at least one electrochemical circuit with the ion—selective analyte sensor. In one embodiment, the sensor 42 configured as the first reference signal source is a solid state reference electrode that is configured so as to not contaminate the sample; and the second reference signal source is an open liquid junction reference sensor, that will contaminate the sample and may be located at a last position within the sensory array assembly 32. In general, the open liquid junction reference sensor is more stable and provides more accurate readings over time than the solid state reference electrode. In accordance with the present disclosure, a sample is passed through the sample flow path and readings are obtained from both the open liquid junction reference sensor and the solid state reference electrode. Then, the reading from the open liquid junction reference sensor is used to calibrate the reading from the solid state reference electrode. Placing the solid state reference electrode upstream of the open liquid junction reference sensor permits samples having a lower sample volume to be passed through the sample flow path 40 as such samples having a lower volume will interact with and be read by at least a subset of the ion-selective analyte sensors and the solid state reference electrode. In this instance, a calibration factor is used to interpret the reading from the solid state reference electrode. The solid state reference electrode may be a polymeric reference electrode.

In one embodiment, the sensor 42a may be a potentiometric sensor for detecting blood urea nitrogen (BUN), the sensor 42b may be the first reference signal source, the sensor 42c may be an amperometric common reference electrode, the sensor 42d may be an amperometric common counter electrode, the sensor 42e may be a potentiometric sensor for detection pH, and the sensor 42g may be a potentiometric sensor for detecting carbon dioxide. Other sensors 42 (not shown) within the sensor array assembly 32 may include an amperometric working electrode, an amperometric counter electrode, an amperometric reference electrode and combinations thereof.

The first signals generated by the sensors 42 are provided to the transducer 36. The transducer 36 is a device that is configured to convert the first signals into second signals with the second signals being another type of energy or form as compared to the first signals. In one embodiment, the transducer 36 is an analog to digital converter. In this embodiment, the first signals are analog electrical signals, and the second signals are digital electrical signals. The second signals are provided to the computing device 38. The computing device 38 receives the second signals and interprets the second signals to determine the presence or absence of analytes within the sample, as discussed below.

The computing device 38 may include one or more suitably programmed processor 39a (e.g., microprocessors) and associated hardware and software, or hardwired logic. The processor 39a may include hardware, e.g., microprocessor, an application specific integrated circuit (ASIC), a field programmable gate array (FPGA), a combination of hardware and software, and/or the like. The term "processor" as used herein means a single processor or multiple processors working independently or together to collectively perform a task or set of tasks.

The computing device 38 may also include one or more computer readable instructions that when executed by the processor 39a perform a specified function. It should be understood that the algorithms described herein may be stored on one or more non-transitory computer readable medium 39b. The non-transitory computer readable medium 39b is coupled to the processor 39a. The computer readable medium 39b may include random access memory, read only memory, flash memory, and/or the like. The non-transitory computer readable medium 39b may be electrically based, optically based, magnetically based, and/or the like.

As illustrated in FIGS. 1, 2A, 2B, and 2C, the sensory array assembly 32 comprises a first sensor body 44 elongated along a longitudinal axis 46. The first sensor body 44 has a first end 48, a second end 50, a first region 52 extending from the first end 48 toward the second end 50, a second region 54 extending from the first region 52 to the second end 50, an inner surface 55a, and an outer surface 55b. In the example shown, the first sensor body 44 supports six of the sensors 42, which are spatially disposed along the inner surface 55a of the first sensor body 44.

The sensory array assembly 32 is also provided with a second sensor body 56 having an inner surface 58, and an outer surface 60. The second sensor body 56 may also be provided with a first end 62 and a second end 64. In one embodiment, the first end 62 is aligned with the first end 48 of the first sensor body 44; and the second end 64 is aligned with the second end 50 of the first sensor body 44.

The first and second sensor bodies 44 and 56 may be made from, for example, ceramic, polymer, foil, or any other type of material known to someone of ordinary skill in the art. The inner surface 55a of the first sensor body 44 and the inner surface 58 of the second sensor body 56 may define the sample flow path 40. The sample flow path 40 may also be defined by two side walls 68a and 68b. The sidewalls 68a and 68b extend along the longitudinal axis 46 of the first sensor body 44 and generally from the first end 48 of the first sensor body 44 toward the second end 50 of the first sensor body 44. In some embodiments, one or more of the sensors 42 may also be provided on the inner surface 58 of the second sensor body 56.

As discussed above, the first sensor body 44 may have the sensors 42 located adjacent to the sample flow path 40. In one embodiment, the sensor 42a is positioned proximate to the first end 48 of the first sensor body 44. At least one of the sensors 42a-g is a first reference signal source and at least one of the sensors 42a-g is an ion selective analyte sensor. The ion-selective analyte sensor includes an electrode that must be used in conjunction with a reference electrode, such as the first reference signal source, to form a complete electrochemical cell. Techniques for making and using an ion-selective analyte sensor are disclosed in U.S. Patent Publication No. 2006/0065527, the entire content of which is hereby incorporated herein by reference. The sensor configured as the first reference signal source can be a polymeric reference electrode that is configured to maintain a relatively constant potential with respect to the sample under the conditions prevailing during a period of time in which the sample is passing through the sample flow path 40. Techniques for making and using a polymeric reference electrode are also disclosed in U.S. Patent Publication No. 2006/0065527, the entire content of which is hereby incorporated herein by reference. Further, the polymeric reference electrode is configured so as to not contaminate the sample and/or the sample flow path 40 when the sample interacts with the polymeric reference electrode. A measured potential difference between the first reference signal source and any of the sensors 42a-f configured as an ion selective analyte sensor can provided to the transducer 36 and used to generate a reading that is forwarded to the computing device 38. In one embodiment, the sensor 42a, and the sensors 42c-42f are ion selective analyte sensors, and the sensor 42b is the first reference signal source. In this embodiment, the first reference signal source (formed by sensor 42b is interlaced between the sensors 42a and 42c. The sample flow path 40 allows the sample to come in contact with the sensors 42a-f In another embodiment, one of the sensors 42 other than the sensor 42b can be the first reference signal source. For example, the sensor 42a or the sensor 42c can be the first reference signal source. In some embodiments, more than one reference signal source can be supplied on the first sensor body 44.

The sensor 42g is within the sample flow path 40, and is configured to form a second reference signal source. The sensor 42g may be configured to maintain a relatively constant potential with respect to the sample under the conditions prevailing during a period of time in which the sample is passing through the sample flow path 40. As will be discussed in more detail below, the sensor 42g may be an open liquid junction reference sensor that contaminates the sample upon interaction between the sample and the open liquid junction reference sensor. By placing the sensor 42g in a last position of the sensor array, any ill effects caused by this contamination is minimized. The open liquid junction reference sensor provides a more accurate reference potential than the solid state reference electrode forming the first reference signal source. Open liquid junction reference sensors are known in the art. Thus, no further details are needed to teach the skilled artisan how to make and use an open liquid junction reference sensor. As discussed below, the sensor 42g may be used to periodically calibrate the first reference signal source so that a reading from the first reference signal source can be used to form a complete electrochemical cell with any of the ion selective analyte sensors discussed herein.

Figure 2A:
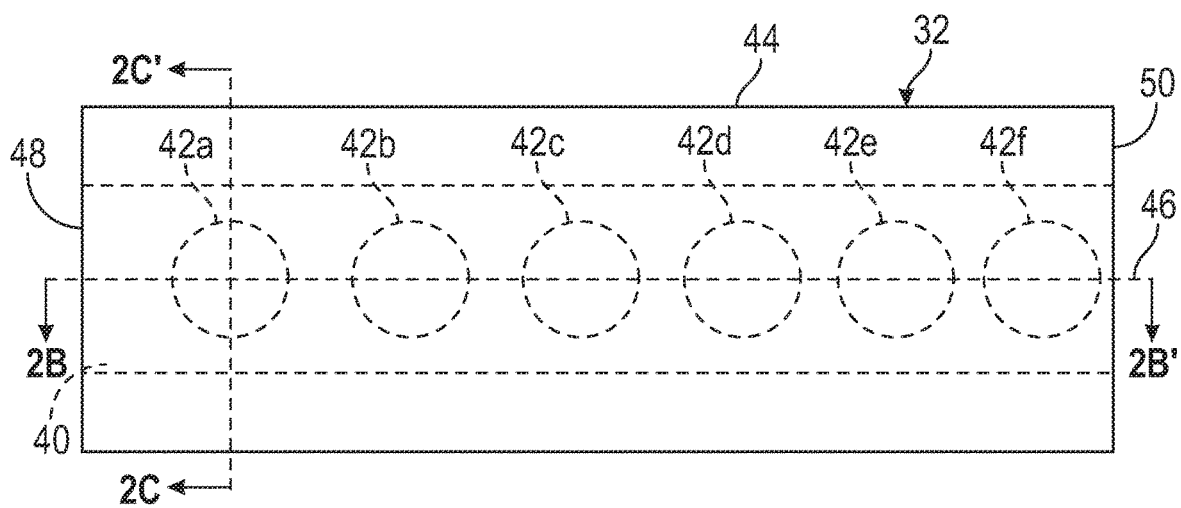
FIG. 2A is a top plan view of a sensor array assembly constructed in accordance with the present disclosure.
Figure 2B:
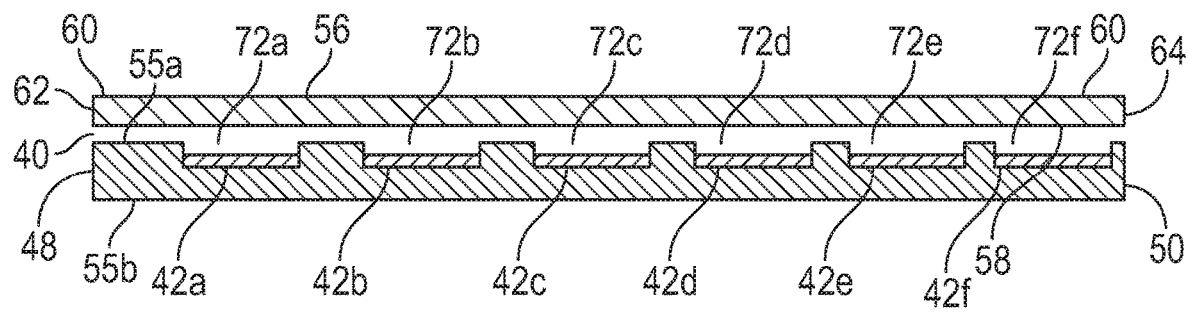
FIG. 2B is a cross-sectional view of the sensor array assembly of FIG. 2A taken along the lines 2B-2B in FIG. 2A.
Figure 2C:
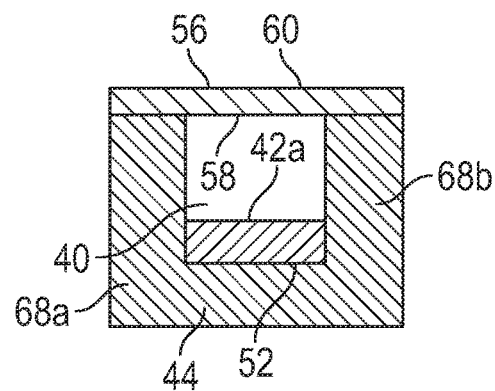
FIG. 2C is a cross-sectional view of the sensor array assembly of FIG. 2A taken along the lines 2C-2C in FIG. 2A.

The sample flow path 40 also has an inlet and an outlet (not shown). The sample flows in through the inlet and out through the outlet in a direction of fluid travel 70 (see FIG. 1). The inlet and/or outlet may be formed in a variety of ways. For example, the inlet and/or outlet may be openings in the side of the first sensor body 44 or may be ports formed in the first end 48 and/or second end 50 of the first sensor body 44. In one embodiment, as shown in FIG. 2B, the inner surface 55a of the first sensor body 44 may be shaped to include reaction wells 72a-f in the sample flow path 40. With the exception of any of the sensors 42a-f configured as the first reference signal source, these reaction wells 72a-f may include a reagent which, in cooperation with the one or more electrical contacts form the sensors 42a-f The sample flow path 40 may take the form of a series of troughs through which the sample flows in the direction of fluid travel 70. The sensory array assembly 32 can be constructed in other ways. For example, the sensory array assembly 32 can be constructed in a manner set forth in U.S. Patent Publication No. 20170203294, the entire content of which is incorporated herein by reference. The sensory array assembly may also be constructed in a manner set forth in WO 2013/163120.

Figure 3A:
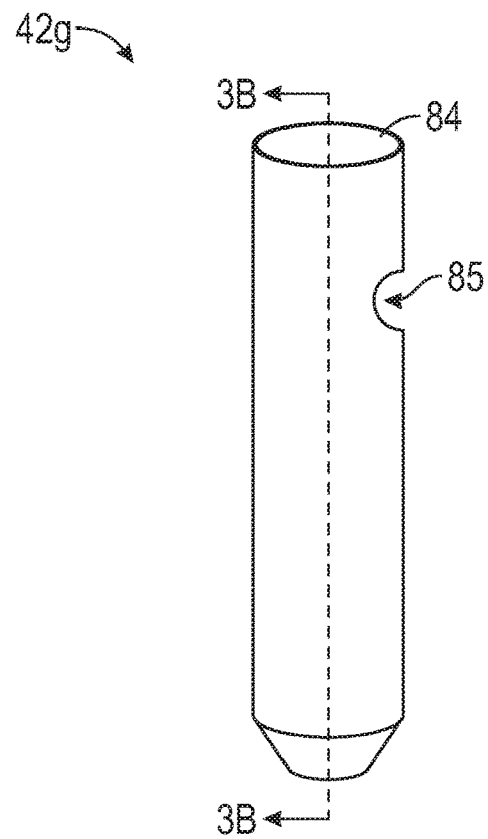
FIG. 3A is a side, perspective view of an exemplary embodiment of a second reference signal source constructed in accordance with the present disclosure.
Figure 3B:
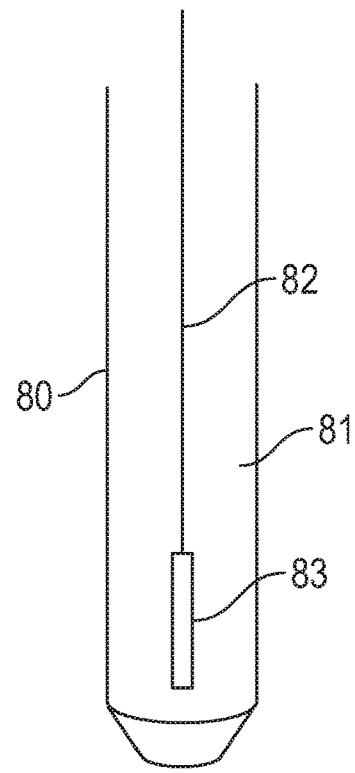
FIG. 3B is a cross-sectional view of the exemplary embodiment of the second reference signal source of FIG. 3A, taken along the lines 3B-3B of FIG. 3A.

FIGS. 3A-3B show an exemplary embodiment of the sensor 42g configured as the second reference signal source.

The sensor 42g may be positioned downstream of the first sensor body 44 and in the sample flow path 40. In one embodiment, the sensor 42g may be separate from the first sensor body 44 and positioned adjacent the second end 50 of the first sensor body 44 (FIG. 1). When the sensor 42g is positioned adjacent to the first sensor body 44, the sample may be conveyed by a conduit 74 forming a part of the sample flow path 40.

As illustrated in FIGS. 3A-3B, the sensor 42g has a container 80, solution 81, wire 82, and internal element 83. The container 80 may have an opening 84, which may be partially open or completely open. The opening 84 may be positioned near the top of the container 80. The sample flows into the container 80 via the opening 84, and reacts with the solution 81 inside the container 80. In one embodiment, the container 80 may have a filling port 85. The filling port 85 may be utilized to supplement the solution 81 within the container 80. In one embodiment, the wire 82 provides an electrical connection between the sensor 42g and the transducer 36. In one embodiment, the sensor 42g may be an open liquid junction reference sensor. Techniques for making and using open liquid junction reference sensors are known in the art. See for example, van den Berg, A., et al. A Micro-Volume Open Liquid-Junction Reference Electrode for pH-ISFETs. Sensors and Actuators B: Chemical, Vol. 1 (January 1990), pp. 425-432.

Figure 4:
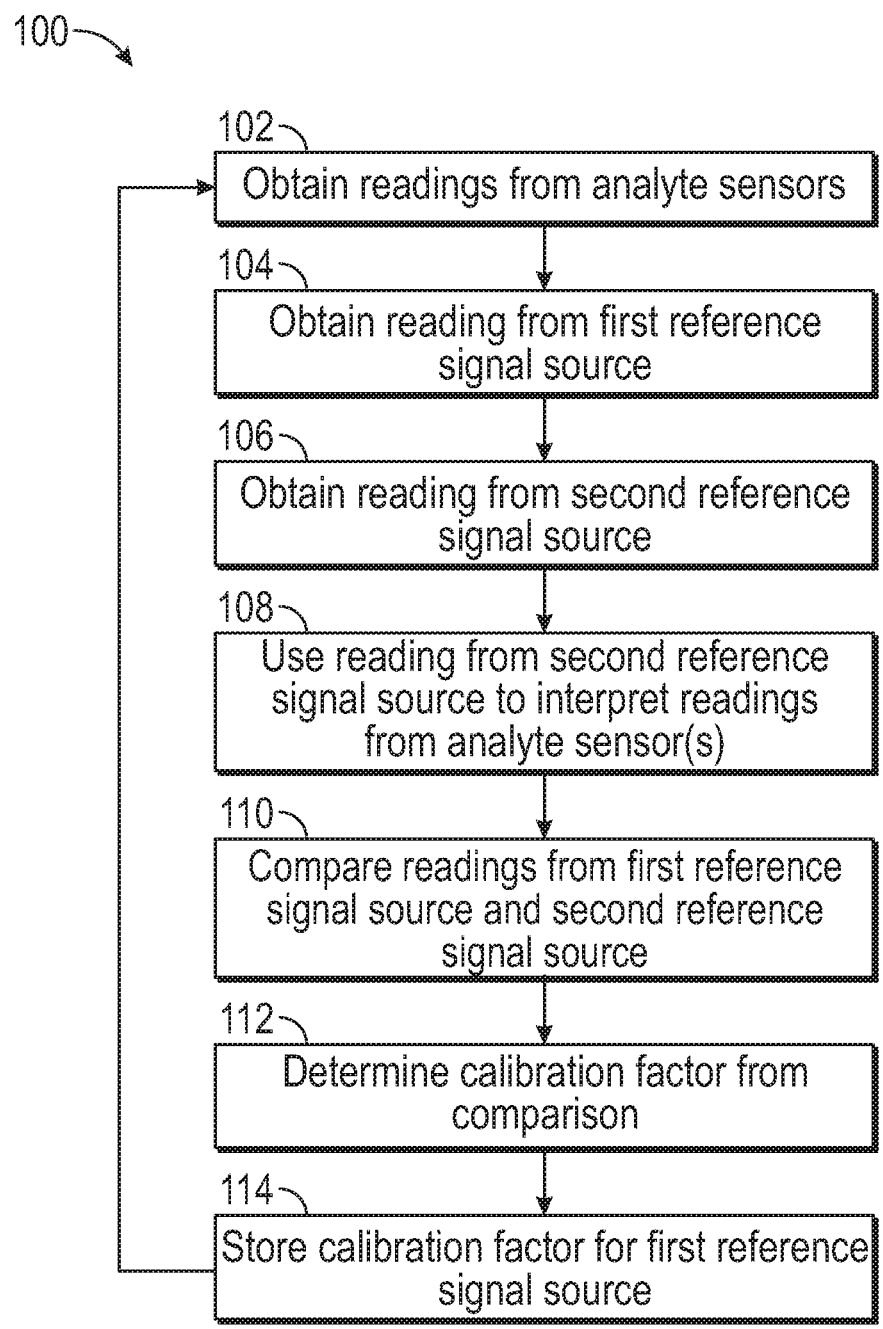
FIG. 4 is a flowchart of an exemplary method for determining a calibration measurement in accordance with one aspect of the present disclosure.

As illustrated in FIG. 4, a method 100 for periodically calibrating the sensor 42b by determining and storing a calibration factor by the processor 39a when a sample (e.g., a first sample) is being passed through the sample flow path 40. In this example, the sensor 42b is the first reference signal source and may be implemented as the solid state reference electrode. Once the sensor 42b is calibrated, the sensor 42b can be used as a reference electrode for interpreting signals generated by the other sensors 42 that are configured as ion selective analyte sensors when subsequent samples (e.g., second samples) are passed through the sample flow path 40. It should be understood that other sensors 42a, and 42c-f could be configured as the first reference signal source rather than the sensor 42b. In this example, however, the sensor 42b will be described as the first reference signal source. At a step 102, the non-transitory computer readable medium 39b stores computer executable instructions that when executed by the processor 39a cause the processor 39a of the computing device 38 to obtain a first reading indicative of one or more analyte within the first sample from at least one of the analyte sensor 42a, or 42c-f exposed to the first sample via the transducer 36. At a step 104, the processor 39a obtains a first reference value of the first sample from the sensor 42b exposed to the first sample. Then, at a step 106, a second reference value is determined for the first sample from the sensor 42g. At a step 108, the processor 39a uses the second reference value to interpret readings from one or more of the sensors 42a, and 42c-f that are configured as ion sensitive analyte sensors. This can be accomplished by determining a difference between the first reading and the second reference value. At a step 110, the first reference value and the second reference value are compared, and then a calibration factor is determined at a step 112 based upon the comparison. This can be accomplished, for example, by subtracting the first reference value from the second reference value. Then, the calibration factor is stored in the non-transitory computer readable medium 39b at a step 114. Once the calibration factor is stored in the non-transitory computer readable medium 39b, the calibration factor may be added to a subsequent reading by the sensor 42b, as the sensor 42b interacts with a second sample.

The method 100 is then repeated so as to periodically calculate the calibration factor to maintain a consistently accurate reading by the sensor 42b.

Figure 5:
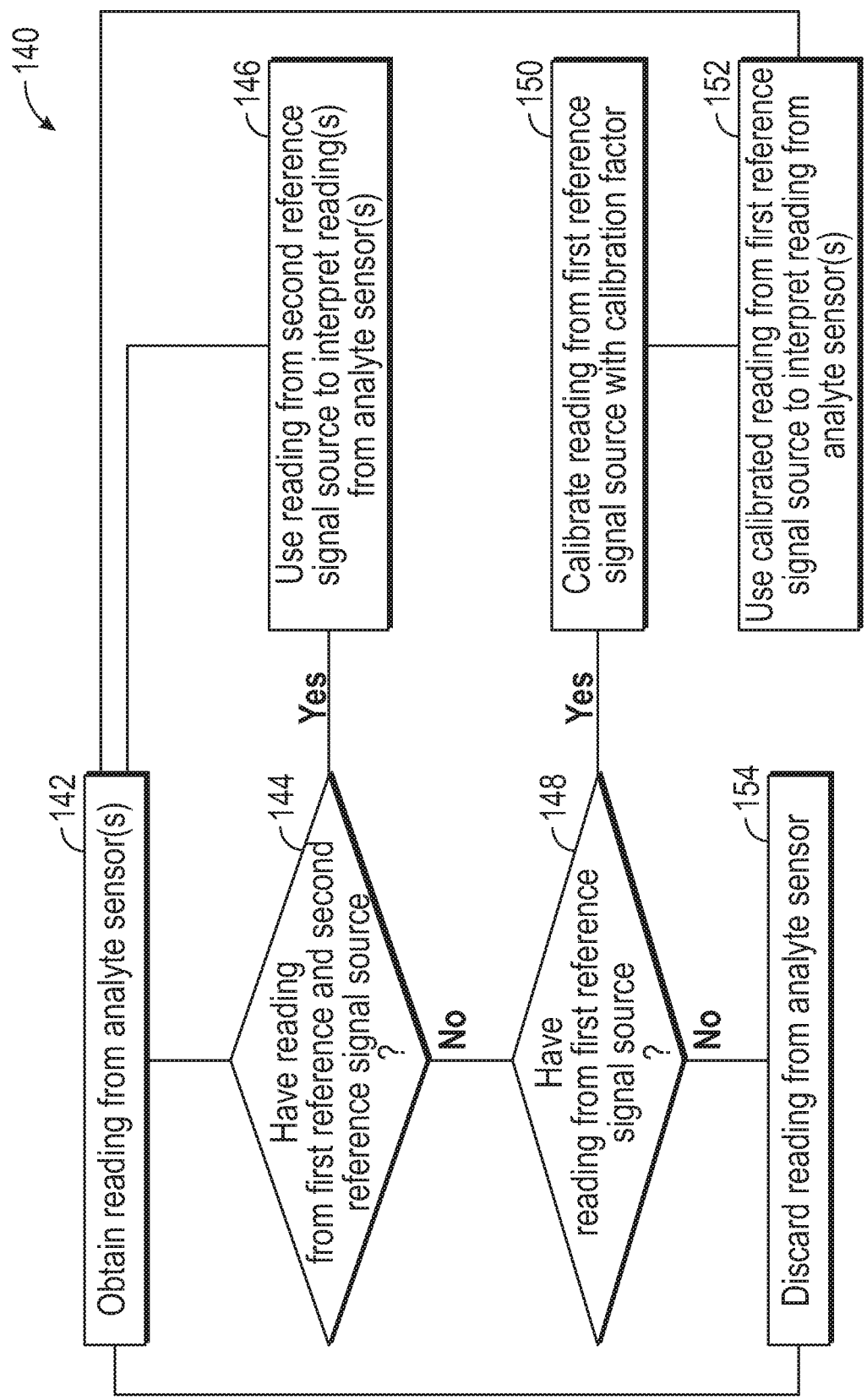
FIG. 5 is a flowchart of an exemplary method for determining the presence or concentration of one or more analyte in accordance with another aspect of the present disclosure.

FIG. 5 illustrates an automated method 140 for determining a presence or concentration of at least one analyte in a sample. The automated method 140 can be implemented with computer executable instructions saved on the non-transitory computer readable medium 39b directing the processor 39a to perform steps, as described below. In this embodiment, the non-transitory computer readable medium 39b has computer executable instructions that when executed by the processor 39a of the computing device 70 causes the processor 39a to pass a sample through the sample flow path 40 such that the sample interacts with at least a subset of the sensors 42 including at least one ion-selective analyte sensor and the first reference signal source. Then, at a step 142, the processor 39a obtains a first reading indicative of one or more of the ion-selective analyte sensors 42a, and 42c-f exposed to the first sample at a step 142, the first reference value from the sensor 42b, and optionally the second reference value from the sensor 42g. The method 140 then branches to a step 144 in which the processor 39a determines whether a reading was obtained from the first reference signal source and the second reference signal source. When a relatively low volume of the sample is passed through the sample flow path 40, then the first reference value may be obtained, but not the second reference value. If the second reference value was obtained, then the method 140 branches to a step 146 in which the second reference value is used to interpret readings from one or more of the ion-selective analyte sensors 42a, and 42c-f. The method 140 then branches to the step 142.

If the second reference value is not obtained, e.g., a low volume sample is passed through the sample flow path 40, then, the method 140 branches to a step 148 where the processor 39a determines whether the first reference value was obtained. If the first reference value was obtained, the method 140 branches to a step 150 where the processor 39a calibrates the first reference value with the calibration factor to form a calibrated reading, and then branches to a step 152 where the calibrated reading is used to interpret readings from the sensors 42a, and 42c-f, for example. Then, the method 140 branches to the step 142.

If the first reference value is not obtained, then the method 140 branches to a step 154 where the processor 39a discards the readings from the sensors 42a, and 42c-f, and then branches to the step 142.

The following is a number list of non-limiting illustrative embodiments of the inventive concept disclosed herein:

1. An analyzer comprising:
   a sensor array assembly, comprising:
   a sensor body elongated along a longitudinal axis, the sensor body having a first end, a second end, a first region extending from the first end toward the second end, a second region extending from the first region to the second end, an inner surface, and an outer surface, the inner surface defining a sample flow path;
   a plurality of sensors intersecting the sample flow path, at least one of the sensors being selective to an ion or ions of interest, at least one of the sensors being a first reference signal source, and at least one of the sensors being a second reference signal source, the second reference signal source being spaced away from the first reference signal source;
   an electronic sensing and control apparatus comprising:
   a computing device configured to receive signals indicative of a first reference value of the first reference signal source, and a second reference value of the second reference signal source and to calibrate the reading of the first reference value with the second reference value.

2. The analyzer of illustrative embodiment 1, wherein the second reference signal source is located outside of the sensor body.

3. The analyzer of any one of illustrative embodiments 1 or 2, wherein the second reference signal source is an open liquid junction reference sensor.

4. The analyzer of any one of illustrative embodiments 1-3, wherein the first reference signal source is at least one of a polymeric or a solid-state reference electrode.

5. The analyzer of any one of illustrative embodiments 1-4, wherein the first reference signal source is positioned within the first region of the sensor body.

6. The analyzer of any one of illustrative embodiments 1-5, wherein the at least one of the sensors includes a first ion-selective electrode, and a second ion-selective electrode and wherein the first reference signal source is interleaved between the first ion-selective electrode and the second ion-selective electrode within the first region of the sensor body.

7. The analyzer of any one of illustrative embodiments 1-6, wherein the at least one of the sensors includes an ion-selective electrode.

8. The analyzer of any one of illustrative embodiments 1-7 wherein the at least one of the sensors being selective to an ion or ions of interest, and at least one of the sensors being a first reference signal source are a part of an electrochemical circuit.

9. A non-transitory computer readable medium storing computer executable instructions that when executed by a processor cause the processor to:
  determine a first reference value of the first sample from a first reference signal source exposed to the first sample;
  determine a second reference value of the first sample from a second reference signal source exposed to the first sample; and
  determine a calibration factor for the first reference signal source using the first and second reference values.

10. The non-transitory computer readable medium storing computer executable instructions that when executed by a computing device of illustrative embodiment 9, further comprises the step of:
  obtain a reading indicative of one or more analyte within a second sample from an ion-selective analyte sensor exposed to the second sample;
  determine a presence or concentration of the one or more analyte within the second sample using a third reference value obtained from the first reference signal source exposed to the second sample, and the calibration factor.

11. The non-transitory computer readable medium storing computer executable instructions that when executed by the processor of any one of illustrative embodiments 9 or 10, cause the processor to:
  determine the calibration factor for the first reference signal source using the first and second reference values by determining a difference between the first and second reference values.

12. The non-transitory computer readable medium storing computer executable instructions that when executed by the processor of illustrative embodiment 9, further comprises the step of:
  obtain a reading indicative of one or more analyte within a second sample from an ion-selective analyte sensor exposed to the second sample;
  determining whether the processor has obtained a third reference value of the second sample from the second reference signal source exposed to the second sample; and
  reading the second sample using the second reading, and the third reference value.

13. A method, comprising:
  passing a first sample through a sample flow path so as to intersect an ion-selective analyte sensor, a first reference signal source, and a second reference signal source, the second reference signal source being downstream from the first reference signal source, the first sample having a first volume;
  determining a presence or concentration of an analyte within the first sample using readings from the ion-selective analyte sensor and the second reference signal source;
  passing a second sample through the sample flow path so as to intersect the ion-selective analyte sensor, and the first reference signal source without intersecting the second reference signal source, the second sample having a second volume less than the first volume; and
  determining a presence or concentration of an analyte within the first sample using readings from the ion-selective analyte sensor and the first reference signal source.

14. The method of illustrative embodiment 13, wherein the first reference signal source is at least one of a polymeric reference electrode or a solid-state reference electrode.

15. The method of any one of illustrative embodiments 13 or 14, wherein the second reference signal source is an open liquid junction reference sensor.

16. The method of any one of illustrative embodiments 13, 14, or 15, further comprising the steps of:
  determine a first reference value of the first sample from the first reference signal source exposed to the first sample;
  determine a second reference value of the first sample from the second reference signal source exposed to the first sample; and
  determine a calibration factor for the first reference signal source using the first and second reference values.

17. The method of illustrative embodiment 16, wherein determining the calibration factor for the first reference signal source includes determining a difference between the first and second reference values.

CONCLUSION

Conventionally, large sample volumes are required to measure an amount, concentration and/or presence of one or more analyte found within a given sample. In accordance with the present disclosure, it is desirable to reduce the amount of liquid sample used to test the liquid sample for the presence and/or the concentration of a variety of analytes. It is to such an improved system and method that the present disclosure is directed.

The foregoing description provides illustration and description, but is not intended to be exhaustive or to limit the inventive concepts to the precise form disclosed. Modifications and variations are possible in light of the above teachings or may be acquired from practice of the methodologies set forth in the present disclosure.

Even though particular combinations of features are recited in the claims and/or disclosed in the specification, these combinations are not intended to limit the disclosure. In fact, many of these features may be combined in ways not specifically recited in the claims and/or disclosed in the specification. Although each dependent claim listed below may directly depend on only one other claim, the disclosure includes each dependent claim in combination with every other claim in the claim set.

No element, act, or instruction used in the present application should be construed as critical or essential to the disclosure unless explicitly described as such outside of the preferred embodiment. Further, the phrase "based on" is intended to mean "based, at least in part, on" unless explicitly stated otherwise.

What is claimed is:

1. An analyzer comprising:
    a sensor array assembly, comprising:
        a sensor body, the sensor body having a first end, a second end, a first region extending from the first end toward the second end, a second region outside of the first region, an inner surface, and an outer surface, the inner surface defining at least a portion of a sample flow path; and
        a plurality of sensors intersecting the sample flow path so as to be exposed to the sample flow path, at least one of the sensors being selective to an ion or ions of interest, at least one of the sensors being a first reference signal source positioned within the first region, and at least one of the sensors being a second reference signal source positioned within the second region, the second reference signal source being downstream from the first reference signal source, the first reference signal source and the second reference signal source being configured to maintain a relatively constant potential reading with respect to a liquid sample under conditions prevailing during a period of time in which the liquid sample is passing though the sample flow path; and
    an electronic sensing and control apparatus comprising:
        a computing device configured to receive signals indicative of a first reference value of the first reference signal source, and a second reference value of the second reference signal source and to calibrate the reading of the first reference value with the second reference value by calculating a calibration factor and to determine a presence or concentration of an analyte within the liquid sample using readings from the ion-selective analyte sensor, the first reference signal source, and the calibration factor.

2. The analyzer of claim 1, further comprising a conduit forming a part of the sample flow path, and wherein the second reference signal source is located outside of the sensor body.

3. The analyzer of claim 1, wherein the second reference signal source is an open liquid junction reference sensor.

4. The analyzer of claim 1, wherein the first reference signal source is at least one of a polymeric or a solid-state reference electrode.

5. The analyzer of claim 1, wherein the at least one of the sensors includes a first ion-selective electrode, and a second ion-selective electrode and wherein the first reference signal source is interleaved between the first ion-selective electrode and the second ion-selective electrode within the first region of the sensor body.

6. The analyzer of claim 1, wherein the at least one of the sensors being selective to an ion or ions of interest, and the at least one of the sensors being the first reference signal source are a part of an electrochemical circuit.

7. A method, comprising:
    passing a first sample through a sample flow path in a sensor body having a first end and a second end so as to expose an ion-selective analyte sensor, a first reference signal source, and a second reference signal source to the first sample, the second reference signal source being downstream from the first reference signal source, the first sample having a first volume;
    determining a presence or concentration of an analyte within the first sample using readings from the ion-selective analyte sensor and the second reference signal source;
    calibrating a first reference value read by the first reference signal source with a second reference value read by the second reference signal source to determine a calibration factor;
    passing a second sample through a portion of the sample flow path so as to expose the ion-selective analyte sensor, and the first reference signal source to the second sample without exposing the second reference signal source to the second sample, the second liquid sample having a second volume less than the first volume; and
    determining a presence or concentration of an analyte within the second sample using readings from the ion-selective analyte sensor and the first reference signal source, and the calibration factor.

8. The method of claim 7, wherein the first reference signal source is at least one of a polymeric reference electrode or a solid-state reference electrode.

9. The method of claim 7, wherein the second reference signal source is an open liquid junction reference sensor.

10. The method of claim 7, wherein calibrating the first reference value with the second reference value further comprises the steps of:
    determine the first reference value of the first sample from the first reference signal source exposed to the first sample;
    determine the second reference value of the first sample from the second reference signal source exposed to the first sample; and
    determine the calibration factor for the first reference signal source using the first and second reference values.

11. The method of claim 10, wherein determining the calibration factor for the first reference signal source includes determining a difference between the first and second reference values.

12. An analyzer comprising:
    a sensor array assembly, comprising:
        a sensor body, the sensor body having a first end, a second end, a first region extending from the first end toward the second end, a second region outside of the first region, an inner surface, and an outer surface, the inner surface defining at least a portion of a sample flow path; and
        a plurality of sensors intersecting the sample flow path so as to be exposed to the sample flow path, at least one of the sensors being selective to an ion or ions of interest, at least one of the sensors being a first reference signal source positioned within the first region, and at least one of the sensors being a second reference signal source positioned within the second region, the second reference signal source being downstream from the first reference signal source, wherein the at least one of the sensors includes a first ion-selective electrode, and a second ion-selective electrode and wherein the first reference signal source is interleaved between the first ion-selective electrode and the second ion-selective electrode within the first region of the sensor body; and an electronic sensing and control apparatus comprising:
  a computing device configured to receive signals indicative of a first reference value of the first reference signal source, and a second reference value of the second reference signal source and to calibrate the reading of the first reference value with the second reference value.

\* \* \* \* \*